(12) United States Patent
Oh

(10) Patent No.: US 9,504,823 B2
(45) Date of Patent: Nov. 29, 2016

(54) MICRO-CURRENT THERAPY DEVICE USING HIGH ELECTRIC POTENTIAL

(71) Applicants: Jaesuk Oh, Yongin-si (KR); Hong Soon Shin, Yongin-si (KR)

(72) Inventor: Jaesuk Oh, Yongin-si (KR)

(73) Assignees: Jaesuk Oh, Yongin-si, Gyeonggi-do (KR); Hong Soon Shin, Yongin-si, Gyeonggi-do (KR)

( * ) Notice: Subject to any disclaimer, the term of this patent is extended or adjusted under 35 U.S.C. 154(b) by 0 days.

(21) Appl. No.: 14/764,566

(22) PCT Filed: Apr. 25, 2014

(86) PCT No.: PCT/KR2014/003661
§ 371 (c)(1),
(2) Date: Jul. 29, 2015

(87) PCT Pub. No.: WO2014/175700
PCT Pub. Date: Oct. 30, 2014

(65) Prior Publication Data
US 2015/0374979 A1 Dec. 31, 2015

(30) Foreign Application Priority Data
Apr. 25, 2013 (KR) ......................... 10-2013-0045807

(51) Int. Cl.
*A61N 1/00* (2006.01)
*A61N 1/08* (2006.01)
(Continued)

(52) U.S. Cl.
CPC . *A61N 1/08* (2013.01); *A61N 1/10* (2013.01); *A61N 1/32* (2013.01)

(58) Field of Classification Search
CPC .......... A61N 1/08; A61N 1/32; A61N 1/322; A61N 1/378; A61N 1/3782
See application file for complete search history.

(56) References Cited

U.S. PATENT DOCUMENTS 5,817,141 A * 10/1998 Iimori ...................... A61N 1/32
607/46
5,913,836 A * 6/1999 Groux ..................... A61N 1/32
601/21

(Continued)

FOREIGN PATENT DOCUMENTS

JP 2002-143324 A 5/2002
JP 2004-243048 A 9/2004

(Continued)

*Primary Examiner* — Robert N Wieland
(74) *Attorney, Agent, or Firm* — Novick, Kim & Lee, PLLC; Jae Youn Kim

(57) ABSTRACT

Provided is a micro-current therapy device using high electric potential to provide high electric potential therapy by generating high electric potential as high voltage induced from a high-voltage transformer, and regulating micro-current of the generated high-electric potential. The micro-current therapy device supplies commercial AC power through a power unit. When a frequency operation signal is inputted through an operation unit, a control unit generates a relay control signal and a high-potential current control signal according to the frequency set by the operation unit. A relay unit supplies or cuts off the commercial AC power supplied from the power unit according to the relay control signal. A high-voltage output unit outputs a high electric potential by boosting up the commercial AC power outputted from the relay unit. A current regulating unit regulates the high electric potential current, thereby applying the optimized high electric potential to a therapy part of a user.

6 Claims, 2 Drawing Sheets

(51) Int. Cl.
  *A61N 1/32*    (2006.01)
  *A61N 1/10*    (2006.01)

(56) References Cited

U.S. PATENT DOCUMENTS

2010/0036464 A1* 2/2010 Picciano .............. A61N 1/0408
                                                       607/66
2010/0198102 A1* 8/2010 Moore .................... A61N 1/32
                                                       600/554

FOREIGN PATENT DOCUMENTS

| JP | 2009-034319 A | 2/2009 |
| JP | 2010-063764 A | 3/2010 |
| KR | 20-0236007 Y1 | 10/2001 |
| KR | 10-0426630 B1 | 4/2004 |
| KR | 10-2010-0035868 A | 4/2010 |
| KR | 10-2012-0043757 A | 5/2012 |
| WO | 94/05370 A1 | 3/1994 |

* cited by examiner

MICRO-CURRENT THERAPY DEVICE USING HIGH ELECTRIC POTENTIAL

TECHNICAL FIELD

The present invention relates to a micro-current therapy device using high electric potential, and more particularly to a micro-current therapy device using high electric potential, capable of supplying high electric potential, which is optimized for a therapy part of a user, to the therapy part of the user by generating the high electric potential as high voltage is induced from a high-voltage transformer, and regulating micro-current of the generated high-electric potential.

BACKGROUND ART

In general, an electric potential therapy appliance artificially forms a vibrant electric field to optimize the state of a human body, and makes the high-voltage potential difference to be indirectly applied to the human body. In other, the potential therapy appliance electrically induces anions necessary for a human body through electrostatic therapy to form a thick anion layer when the human body makes contact with an electric potential plate. Through the action of the thick anion layer, the blood of the human body can be prevented from being acidified by effectively using minerals existing in the blood and the blood can be maintained in an alkalescence state, so that the disease can be prevented and the resistance to the disease can be enhanced.

In other words, the electric potential therapy appliance forms the thick anion layer around the human body using the high-voltage potential difference to activate a cell function, ionizes the inner part of the human body to increase an amount of waste discharged from the human body, and accelerates the metabolic function of the human body. In addition, the electric potential therapy appliance changes the acidified blood to ideal alkalescence blood to improve the human body so that the human body has a strong constitution with resistance to diseases, removes cholesterol from an artery wall while enlarging a peripheral blood vessel to smoothly circulate blood, thereby preventing a chronic disease, such as hypertension and diabetes, and adjusts the automatic nervous system to improve the regulation of an endocrine function.

The electric potential therapy appliance mainly employs a high voltage transformer to generate high voltage in order to artificially form a vibrant electric field.

Electric potential therapy apparatuses according to the related arts are disclosed in Korea Utility Model Registration No. 20-0236007 (issued on Oct. 8, 2001, related art 1), Korea Unexamined Patent Publication No. 10-2010-0035868 (published on Apr. 7, 2010, related art 2) and Korean Unexamined Patent Publication No. 10-2012-0043757 (published on May 4, 2012, related art 3).

According to the related art 1, high voltage is generated using a transformer, and differentially output from a potential generator, and strong, middle or weak voltage is applied to a pain part using the differentially output voltage by an electronic acupuncture.

In addition, according to the related art 2, when several electric potential therapy apparatuses are installed, the electric potential therapy apparatuses are maintained in-phase, thereby preventing a danger such as the high-voltage electric shock.

Further, the related art 3 provides an electric potential therapy apparatus having a simplified structure and prevented from being deteriorated.

However, according to the relate arts, although high voltage for the electric potential therapy can be generated, the high electric potential current cannot be selectively regulated according to the therapy part of a user.

In other words, despite the possibility that the quantity of high electric potential current can be adjusted according to the state of the therapy part of the user to produce the optimal therapy effect, the adjustment of the high electric potential current appropriate to the state of the therapy part is difficult according to the above related arts, so that the optimal therapy effect may not be produced.

DISCLOSURE

Technical Problem

The present invention is suggested to solve the problems occurring in the related art, and an object of the present invention is to provide a micro-current therapy device using high electric potential, capable of supplying high electric potential, which is optimized for a therapy part of a user, to the therapy part of the user by generating the high electric potential as high voltage is induced from a high-voltage transformer, and regulating the micro-current of the generated high-electric potential.

Another object of the present invention is to provide a micro-current therapy device using high electric potential, capable of performing a therapy for a deep part of a user by changing a frequency in multiple stages according to the states of a therapy part of the user.

Technical Solution

In order to accomplish the above objects, there is provided a micro-current therapy device using high electric potential. The micro-current therapy device includes a power supply unit to supply commercial AC power, an operating unit to input a frequency operation signal, a control unit to generate a relay control signal and a high electric potential current control signal according to a frequency set by the operating unit, a relay unit to supply or cut off the commercial AC power supplied from the power supply unit according to the relay control signal generated from the control unit, a high-voltage output unit to output the high electric potential by boosting up the commercial AC power output from the relay unit, and a current-regulating unit to regulate high electric potential current, which is output from the high-voltage output unit, according to the current control signal generated from the control unit.

The frequency operation signal corresponds to 15 Hz, 30 Hz, 60 Hz, 90 Hz, or 180 Hz.

The control unit recognizes the state of the therapy part of the user based on the frequency set by the operating unit, and generates the current control signal corresponding to the recognized state of the therapy part of the user.

The current-regulating unit includes a switch to perform a switching operation according to the current control signal generated from the control unit, and a plurality of current regulators to differentially regulate the high electric potential current output from the high-voltage output unit according to the switching operation of the switch.

Each current regulator includes a resistor.

In addition, the micro-current therapy device according to an exemplary embodiment of the present invention further includes a high-voltage cutoff unit interposed between the current-regulating unit and the high-voltage output unit to cut off the output of the high electric potential if the high electric potential current output from the high-voltage output unit exceeds preset current, and a display unit to visually display a frequency level state and an operation state set by the user according to control of the control unit.

The high-voltage cutoff unit includes a fuse.

Advantageous Effects

As described above, according to the present invention, the high electric potential is generated by inducing the high voltage from the high voltage transformer, and the generated high electric potential can be micro-current regulated, thereby supplying the high electric potential, which is optimized for the state of the therapy part of the user, to the therapy part of the user.

In addition, according to the present invention, the high electric potential can be applied to the deep part of the user by changing the frequency in multiple stages according to the states of the therapy part of the user. Accordingly, the aggregation of mineral ingredients can be increased, and the reparative power of nature can be enhanced.

BEST MODE

Mode for Invention

Hereinafter, an exemplary embodiment of the present invention will be described in detail with reference to accompanying drawings. Prior to the description of the present invention, if detailed description about well-known functions or configurations may make the subject matter of the present invention unclear, the detailed description of the well-known functions or configurations will be omitted.

Figure 1:
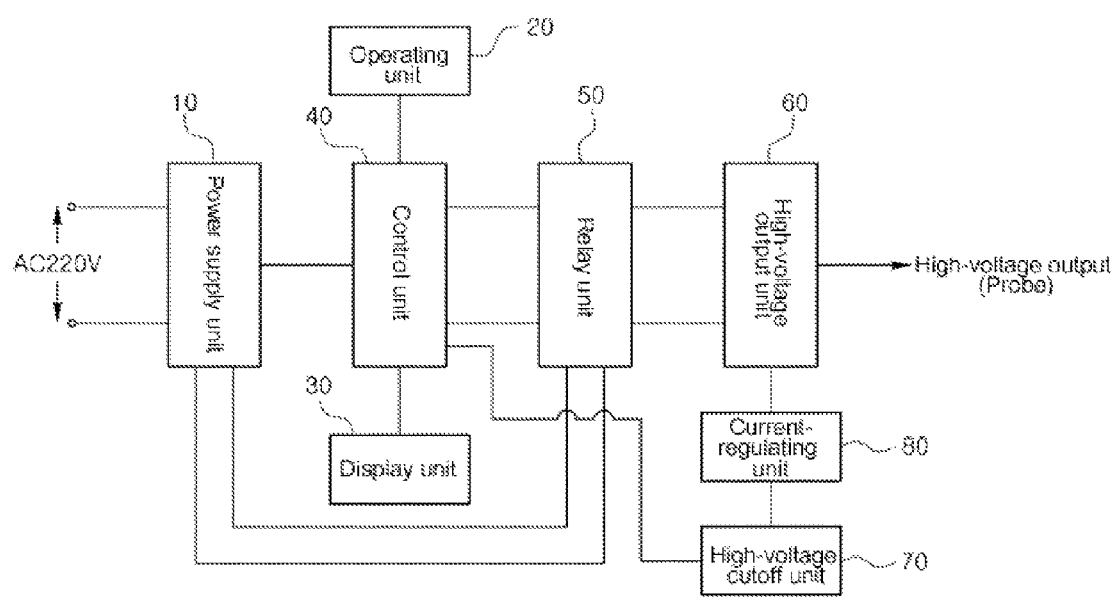
FIG. 1 is a block diagram showing a micro-current therapy device using high electric potential according to an exemplary embodiment of the present invention.
Figure 2:
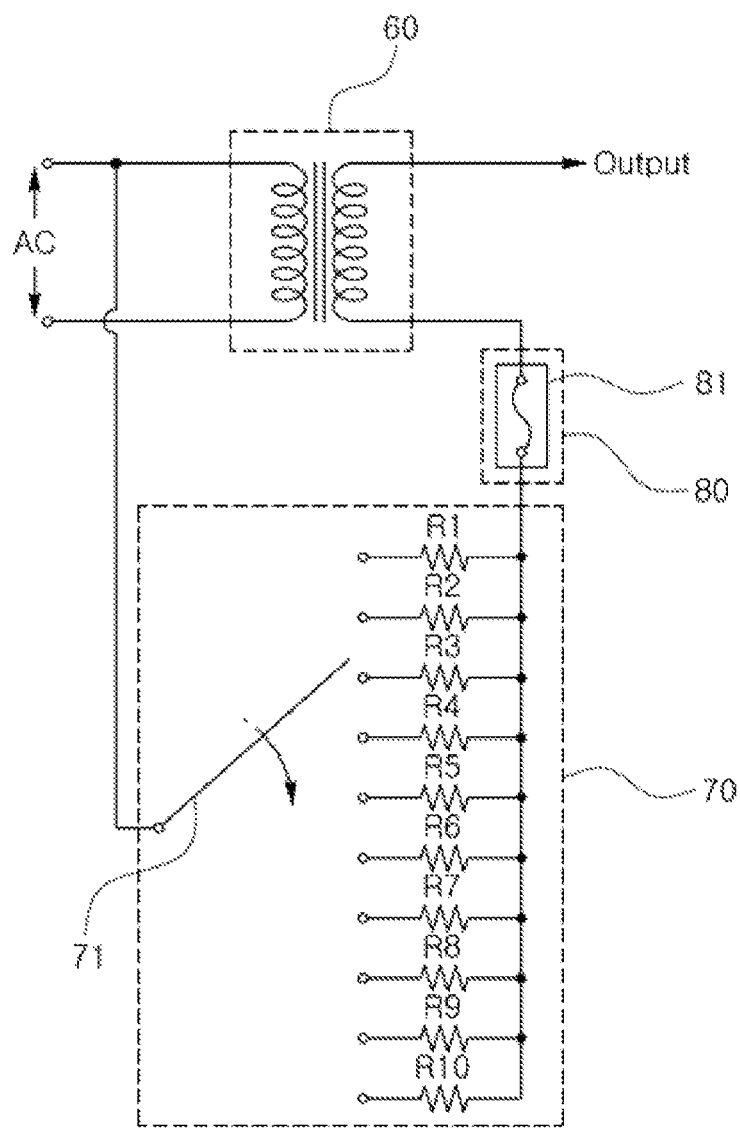
FIG. 2 is a circuit diagram showing a high-voltage output unit, a high-voltage cutoff unit, and a current-regulating unit of FIG. 1 according to the embodiment.

FIG. 1 is a block diagram showing a micro-current therapy device using high electric potential according to an exemplary embodiment of the present invention. FIG. 2 is a circuit diagram showing a high-voltage output unit, a high-voltage cutoff unit, and a current-regulating unit of FIG. 1 according to the embodiment.

As shown in FIGS. 1 and 2, the micro-current therapy device using high electric potential according to the present invention includes a power unit 10, an operating unit 20, a display unit 30, a control unit 40, a relay unit 50, a high-voltage output unit 60, a high-voltage cutoff unit 80, and a current-regulating unit 70.

The power supply unit 10 supplies input commercial AC power (AC220V), makes predetermined DC voltage through full wave rectification, and supplies driving voltage to the control unit 40.

The operating unit 20 inputs a frequency operating signal, which is manipulated by a user, to the control unit 40. In this case, the frequency operating signal may correspond to 15 Hz, 30 Hz, 60 Hz, 90 Hz, or 180 Hz.

The control unit 40 generates a relay control signal and a high electric potential current control signal according to the frequency set by the operating unit 20. The control unit 40 is preferably realized in the form of a controller such as a micro-processor, a micro-computer, a controller, or a central process unit. In addition, the control unit 40 preferably includes a data storage device to store control data used to generate the current control signal corresponding to the set frequency.

The relay unit 50 supplies or cut offs the commercial AC power supplied from the power supply unit 10 according to the relay control signal generated from the control unit 40. The relay unit 50 preferably includes a relay coil and a relay switch.

The high-voltage output unit 60 outputs the high electric potential by boosting up the commercial AC power output from the relay unit 50. The high-voltage output unit 60 preferably includes a high voltage transformer which receives the commercial AC voltage at a primary side and induces the commercial AC voltage to a secondary side to output high voltage (3,000V). In this case, the winding ratio between the primary and secondary sides of the high voltage transformer is set depending on the high electric potential to be output.

The current-regulating unit 70 regulates high electric potential current, which is output from the high-voltage output unit 60, according to the current control signal generated from the control unit 40. The current-regulating unit 70 preferably includes a switch 71 to perform a switching operation according to the current control signal generated from the control unit 40, and a plurality of current regulators R1 to R10 to differentially regulate the high electric potential current output from the high-voltage output unit 60 according to the switching operation of the switch 71.

The high-voltage cutoff unit 80 is interposed between the current-regulating unit 70 and the high-voltage output unit 60 to cut off the output of the high electric potential if the high electric potential current output from the high-voltage output unit 60 exceeds preset current. The high-voltage cutoff unit 80 preferably includes a fuse 81.

The display unit 30 visually displays a frequency level state and an operation state set by the user according to control of the control unit 40.

Hereinafter, the operation of the micro-current therapy device using high electric potential according to the present invention, which is configured above, will be described in detail with reference to FIGS. 1 and 2.

First, a user sets a frequency through the operating unit 20 according to the state of the part of the user to be subject to high electric potential therapy. In this case, the frequency may be set to 15 Hz, 30 Hz, 60 Hz, 90 Hz and 180 Hz. According to the frequency setting scheme, the frequency may be set by individually realizing a button corresponding to each frequency and operating the relevant button. According to another scheme, up and down buttons are provided. If the up button is pressed, a frequency is increased from a present frequency step by step. If the down button is pressed, the frequency is decreased from the present frequency step by step.

If the frequency is set according to the state of the therapy part of the user through the operating unit 20, the control unit 40 recognizes the frequency, generates the current control signal corresponding to the set frequency based on the control data stored in the internal data storage device, and transmits the current control signal to the current-regulating unit 70. For example, the data storage device stores a control table in which a frequency is matched with a current control signal corresponding to the frequency. Thereafter, if the user varies the frequency through the operating unit 20, the control unit 40 immediately extracts the current control signal through the control table. In the present invention, five frequencies may be set for the convenience of explanation, and ten current control signals are provided according to the set frequencies. Actually, a control operation is possible when the number of set frequencies is matched with the number of current control signals in one-to-one relationship. However, according to the present invention, two upper and lower current control signals may be used as one frequency is set. For example, on the assumption that a fifth current control signal corresponds to a present frequency, a sixth current control signal and a seventh current control signal are alternately used by increasing the present frequency by one step. In this case, since the increase and the decrease in the intensity of the potential provided for the user are repeated, a more effective therapy can be obtained as compared with the therapy using one intensity of the potential. The fifth, sixth, and seventh current control signals refer to that relevant current regulators are selected from among the current regulators shown in FIG. 2.

In this case, the level of the frequency set according to the operation of the user is displayed through the display unit 30, so that the user can easily recognize a present level of the frequency.

Meanwhile, if the operating switch is manipulated in the state that the frequency is set, the power supply unit 10 performs the full wave rectification and smoothing with respect to the commercial AC power to form predetermined DC voltage and supply the driving voltage to the control unit 40 while supplying the input commercial AC power to the relay unit 50.

If the operating switch is turned on, the control unit 40 generates the relay control signal to drive the relay unit 50 while generating the current control signal corresponding to the set frequency to transmit the current control signal to the current-regulating unit 70.

The relay unit 50 is operated according to the applied relay control signal to supply the commercial AC power, which is supplied from the power supply unit 10, to the high-voltage output unit 60.

The high-voltage output unit 60 induces the high voltage input to the primary side to the secondary side using the high voltage transformer to generate the high electric potential.

In this case, the current-regulating unit 70 selects a specific current regulator among a plurality of regulators, which are stored, as the switch 71 is operated according to the current control signal generated from the control unit 40. For example, the current control signal generated from the control unit 40 determines a movement degree of the switch 71, and the position of the switch 71 is changed by the movement degree of the switch 71 so that the switch 71 is connected with any one of the current regulators. In this case, the high electric potential current to be output from the high-voltage output unit 60 is adjusted by the resistor connected with the connection line of the switch 71. In this case, the current regulator is realized in the form of a resistor. The resistor adjusts the current. Accordingly, if the resistors R1 to R10 are set to mutually different resistances, the quantity of the output high electric potential current is varied corresponding to the relevant resistor. For example, the resistors R1 to R10 may be set to 1 M$\Omega$, 2 M$\Omega$, 3 M$\Omega$, 4 M$\Omega$, 5 M$\Omega$, 6 M$\Omega$, 7 M$\Omega$, 8 M$\Omega$, 9 M$\Omega$, and 10 M$\Omega$, respectively. Accordingly, the high electric current can be differentially adjusted to a value of 0.3 mA to 0.03 mA.

The quantity of the high electric potential current output to a probe can be adjusted corresponding to the state of the therapy part of the user through the above principle. The quantity of the micro-current can be adjusted so that the optimal therapy effect can be produced. For example, in the case of a pain or inflammation is severe in the part of the user to be subject to the therapy, the quantity of the high electric potential current is increased to enhance the therapy effect. Otherwise, in the case of the pain or the inflammation is weak in the part of the user to be subject to the therapy, the quantity of the high electric potential current is decreased to apply a small amount of impact to the user while optimizing the therapy effect.

Meanwhile, according to the present invention, in order to protect the user from the high electric potential current or prevent the probe from being abnormal, the high-voltage cutoff unit 80 is employed. The high-voltage cutoff unit 80 includes the fuse 81 to automatically disconnect the fuse 81 if the high electric potential current exceeds preset current. If the fuse 81 is automatically disconnected due to the overcurrent, the high voltage output is cut off to protect the human body.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

The invention claimed is:

1. A micro-current therapy device using high electric potential, which performs a therapy using the high electric potential, the micro-current therapy device comprising:
    a power supply unit to supply commercial AC power;
    an operating unit to input a frequency operation signal corresponding to a state of a therapy part of a user;
    a control unit to generate a relay control signal and a high electric potential current control signal according to a frequency set by the operating unit;
    a relay unit to supply or cut off the commercial AC power supplied from the power supply unit according to the relay control signal generated from the control unit;
    a high-voltage output unit to output the high electric potential by boosting up the commercial AC power output from the relay unit; and
    a current-regulating unit to regulate high electric potential current, which is output from the high-voltage output unit, corresponding to the state of the therapy part of the user according to the current control signal generated from the control unit,
    wherein the current-regulating unit comprises:
    a switch to perform a switching operation according to the current control signal generated from the control unit; and
    a plurality of current regulators to differentially regulate the high electric potential current output from the high-voltage output unit according to the switching operation of the switch.

2. The micro-current therapy device of claim 1, wherein the frequency operation signal corresponds to 15 Hz, 30 Hz, 60 Hz, 90 Hz, or 180 Hz.

3. The micro-current therapy device of claim 1, wherein the control unit recognizes the state of the therapy part of the user based on the frequency set by the operating unit, and generates the current control signal corresponding to the recognized state of the therapy part of the user.

4. The micro-current therapy device of claim 1, wherein each current regulator comprises a resistor.

5. The micro-current therapy device of claim 1, further comprising:
    a high-voltage cutoff unit interposed between the current-regulating unit and the high-voltage output unit to cut off the output of the high electric potential if the high electric potential current output from the high-voltage output unit exceeds preset current; and a display unit to visually display a frequency level state and an operation state set by the user according to control of the control unit.

6. The micro-current therapy device of claim 5, wherein the high-voltage cutoff unit comprises a fuse.

\* \* \* \* \*